United States Patent
Okusawa et al.

(10) Patent No.: US 10,130,240 B2
(45) Date of Patent: Nov. 20, 2018

(54) MEDICAL SYSTEM

(71) Applicant: OLYMPUS CORPORATION, Hachioji-shi, Tokyo (JP)

(72) Inventors: Yasuhiro Okusawa, Higashimurayama (JP); Kuniaki Kami, Hachioji (JP); Koichi Tashiro, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/228,389

(22) Filed: Aug. 4, 2016

(65) Prior Publication Data

US 2016/0338570 A1   Nov. 24, 2016

Related U.S. Application Data

(63) Continuation of application No. PCT/JP2015/060363, filed on Apr. 1, 2015.

(30) Foreign Application Priority Data

Aug. 4, 2014 (JP) .................................. 2014-158917

(51) Int. Cl.
*A61B 1/00* (2006.01)
*A61B 1/06* (2006.01)
(Continued)

(52) U.S. Cl.
CPC ........ *A61B 1/00006* (2013.01); *A61B 1/0005* (2013.01); *A61B 1/00009* (2013.01);
(Continued)

(58) Field of Classification Search
CPC ............ A61B 1/00006; A61B 1/00009; A61B 1/0661; A61B 1/0669; A61B 1/0684;
(Continued)

(56) References Cited

U.S. PATENT DOCUMENTS

| | | |
|---|---|---|
| 2003/0046562 A1 | 3/2003 | Uchikubo |
| 2004/0204627 A1 | 10/2004 | Furukawa |
| 2005/0215854 A1 | 9/2005 | Ozaki et al. |
| 2008/0091065 A1 | 4/2008 | Oshima et al. |

FOREIGN PATENT DOCUMENTS

| | | |
|---|---|---|
| JP | 2004-105533 A | 4/2004 |
| JP | 2004-165728 A | 6/2004 |

(Continued)

OTHER PUBLICATIONS

May 10, 2016 Decision to Grant issued in Japanese Patent Application No. 2015-562975.
(Continued)

*Primary Examiner* — Timothy J Neal
*Assistant Examiner* — Aaron B Fairchild
(74) *Attorney, Agent, or Firm* — Oliff PLC

(57) ABSTRACT

A medical system includes a light source apparatus, an operating field monitor, and a system controller. The system controller includes a discriminating section and a control section configured to perform control to display, when an endoscopic image is displayed on the operating field monitor, a voice operation main screen for instructing operation of a controlled apparatuses and the endoscopic image on the operating field monitor and display, when the endoscopic image is not displayed on the operating field monitor, a voice operation screen for performing a check of operation states of the controlled apparatuses and an operation instruction of the controlled apparatuses on the operating field monitor.

8 Claims, 5 Drawing Sheets

(51) Int. Cl.
  *A61B 34/00*  (2016.01)
  *A61B 90/00*  (2016.01)
  *A61B 1/05*   (2006.01)
  *A61B 1/07*   (2006.01)
  *A61B 18/00*  (2006.01)
  *A61B 90/30*  (2016.01)
  *A61B 34/10*  (2016.01)
  *A61B 17/00*  (2006.01)

(52) U.S. Cl.
  CPC ...... *A61B 1/00039* (2013.01); *A61B 1/00045* (2013.01); *A61B 1/05* (2013.01); *A61B 1/07* (2013.01); *A61B 34/25* (2016.02); *A61B 90/37* (2016.02); *A61B 1/0661* (2013.01); *A61B 34/10* (2016.02); *A61B 90/30* (2016.02); *A61B 2017/00203* (2013.01); *A61B 2018/00982* (2013.01); *A61B 2034/254* (2016.02); *A61B 2090/3612* (2016.02); *A61B 2090/372* (2016.02); *A61B 2560/0437* (2013.01)

(58) Field of Classification Search
  CPC ... A61B 1/07; A61B 1/00045; A61B 1/00039; A61B 1/0676
  See application file for complete search history.

(56) References Cited

FOREIGN PATENT DOCUMENTS

| | | |
|---|---|---|
| JP | 2006-288955 A | 10/2006 |
| JP | 2007-175231 A | 7/2007 |
| JP | 2008-086666 A | 4/2008 |
| JP | 2012-065698 A | 4/2012 |

OTHER PUBLICATIONS

Jun. 16, 2015 International Search Report issued in Patent Application No. PCT/JP2015/060363.

Oct. 10, 2017 Extended European Search Report issued in European Patent Application No. 15829391.0.

MEDICAL SYSTEM

CROSS REFERENCE TO RELATED APPLICATION

This application is a continuation application of PCT/JP2015/060363 filed on Apr. 1, 2015 and claims benefit of Japanese Application No. 2014-158917 filed in Japan on Aug. 4, 2014, the entire contents of which are incorporated herein by this reference.

BACKGROUND OF THE INVENTION

1. Field of the Invention

The present invention relates to a medical system and, more particularly, to a medical system that centrally controls a plurality of apparatuses.

2. Description of the Related Art

In recent years, according to development of technologies, types of medical apparatus have become abundant and functions of the medical apparatuses have become satisfying. In an operating room, besides these medical apparatuses, various apparatuses such as a room light, various display apparatuses, an endoscope that picks up medical images, and a recording apparatus are disposed. A medical system that centrally controls and manages various medical apparatuses including these apparatuses with a central control apparatus (a system controller) has also been developed.

In the central control apparatus of the medical system of this type, in general, parameters and the like of controlled apparatuses are set and changed by an operation panel that receives touch signals. The operation panel is often placed on a rack or a trolley set in an unclean region. A surgeon often cannot directly operate the operation panel. Therefore, a method of issuing an instruction to a nurse or the like always present in the unclean region and causing the nurse to operate the operation panel on behalf of the surgeon has been used.

During a surgical operation, the surgeon performs a manipulation while viewing an operating field monitor on which medical images such as endoscopic images are projected and gives operation instructions for the controlled apparatuses to the nurse and the like according to necessity. The nurse operates the operation panel and performs setting and changes of parameters and the like of the controlled apparatuses according to the instructions from the surgeon (see, for example, Japanese Patent Application Laid-Open Publication No. 2007-175231).

SUMMARY OF THE INVENTION

A medical system according to an aspect of the present invention includes: a light source apparatus configured to supply a light source for obtaining an endoscopic image into a body cavity; a display apparatus configured to display the endoscopic image; and a control apparatus configured to control a plurality of controlled apparatuses. The control apparatus includes: a discriminating section configured to discriminate whether the endoscopic image is displayed on the display apparatus; and a control section configured to perform control to display, when it is discriminated by the discriminating section that the endoscopic image is displayed on the display apparatus, a first operation instruction screen for instructing operation of the controlled apparatuses and the endoscopic image on the display apparatus and display, when it is discriminated by the discriminating section that the endoscopic image is not displayed on the display apparatus, a second operation instruction screen for performing a check of operation states of the controlled apparatuses and an operation instruction of the controlled apparatuses on the display apparatus.

A medical system according to an aspect of the present invention includes: a light source apparatus configured to supply a light source for obtaining an endoscopic image into a body cavity; a display apparatus configured to display the endoscopic image; and a control apparatus configured to control a plurality of controlled apparatuses, wherein the control apparatus includes: a discriminating section configured to discriminate whether the endoscopic image is displayed on the display apparatus; and a control section configured to perform control to display, when it is discriminated by the discriminating section that the endoscopic image is not displayed on the display apparatus, an operation instruction screen for performing a check of operation states of the controlled apparatuses and an operation instruction of the controlled apparatuses on the display apparatus.

DETAILED DESCRIPTION OF THE PREFERRED EMBODIMENT(S)

An embodiment is explained with reference to the drawings.

Figure 1:
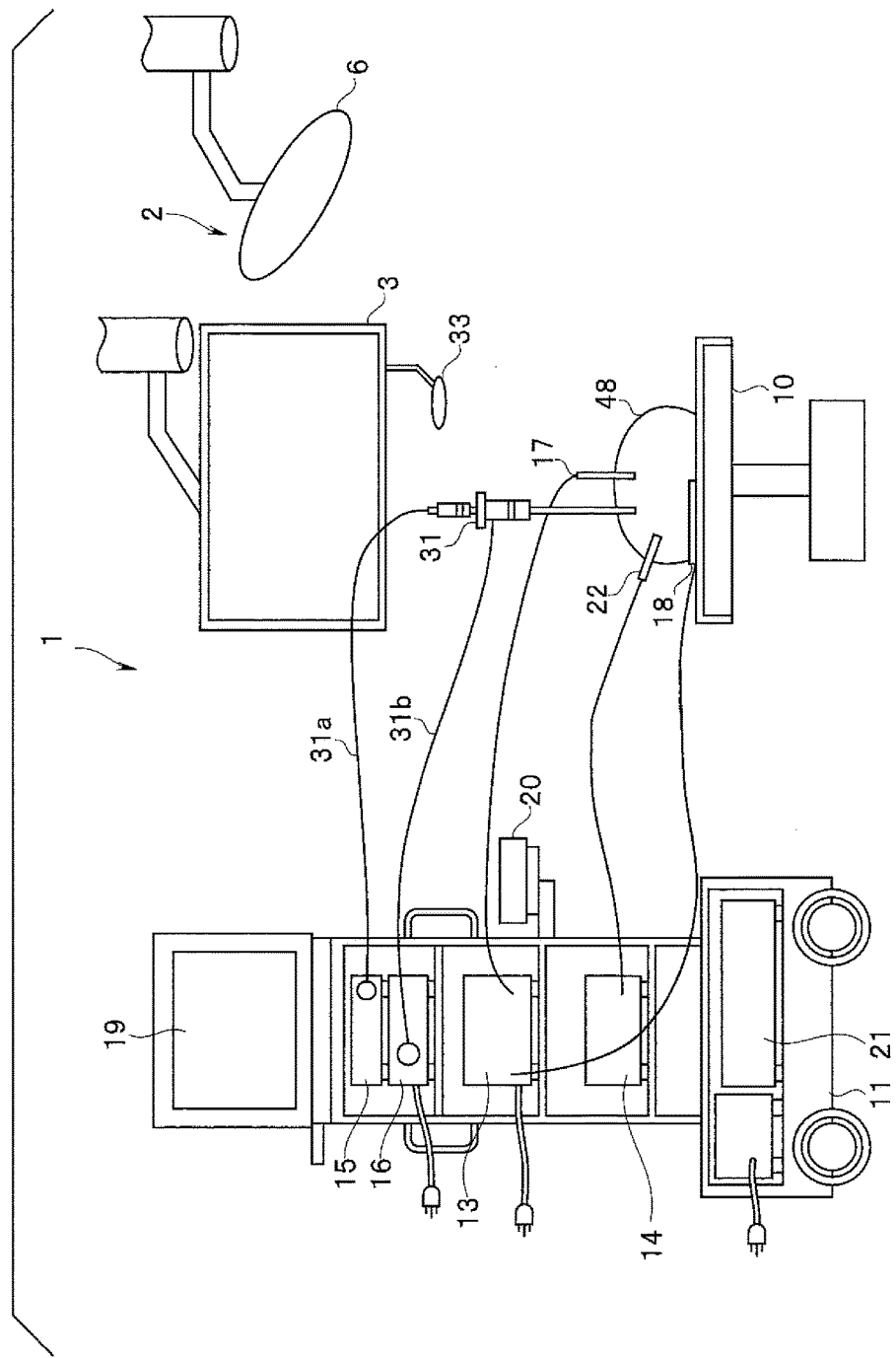
FIG. 1 is a diagram for explaining an example of an overall configuration of a medical system 1 according to an embodiment of the present invention.

FIG. 1 is a diagram for explaining an example of an overall configuration of a medical system 1 according to an embodiment of the present invention. As shown in FIG. 1, the medical system 1 in the present embodiment is disposed in an operating room 2. In the operating room 2, a patient bed 10 on which a patient 48 lies, a shadowless lamp 6, and the like are disposed together with the medical system 1. The medical system 1 includes a trolley 11 on which apparatuses such as an electric knife apparatus 13, a pneumoperitoneum apparatus 14, a camera apparatus for endoscope 15, and a light source apparatus 16 are placed as medical apparatuses, which are controlled apparatuses.

A system controller 21, which is a central control apparatus, is also placed on the trolley 11. The shadowless lamp 6, the electric knife apparatus 13, the pneumoperitoneum apparatus 14, the camera apparatus for endoscope 15, and the light source apparatus 16 are connected to the system controller 21 via a not-shown communication line. An operating field monitor 3 set in a sterilized region is also connected to the system controller 21 via a not-shown signal line.

The operating field monitor 3 is a display apparatus such as a liquid crystal display. A video signal inputted from the camera apparatus for endoscope 15 via the system controller 21, that is, an endoscopic image or the like of a diseased part or the like is displayed. On the operating field monitor 3, not only the endoscopic image but also an operation instruction screen for controlling the respective apparatuses connected to the system controller 21 can be displayed.

The electric knife apparatus 13 is connected to an active electrode 17 and a patient plate 18 set under a body of the patient 48 and performs cauterization of a body surface, the diseased part, and the like. A not-shown carbon dioxide gas cylinder is connected to the pneumoperitoneum apparatus 14. Carbon dioxide gas is supplied into an abdomen of the patient 48 via a trocar 22.

The camera apparatus for endoscope 15 is connected to an endoscope 31 via a camera cable 31a. A camera head including an image pickup device is mounted on a proximal end side of an insertion section of the endoscope 31. An optical image of the diseased part or the like is picked up by the image pickup device in the camera head. A picked-up image signal picked up by the image pickup device is transmitted to the camera apparatus for endoscope 15 via the camera cable 31a. The camera apparatus for endoscope 15 applies predetermined signal processing to the transferred picked-up image signal and generates a video signal. The camera apparatus for endoscope 15 outputs the generated video signal to the operating field monitor 3 and a central display panel 19 via the system controller 21.

The light source apparatus 16 is connected to the endoscope 31 via a light guide cable 31b for transmitting illumination light irradiated from a lamp 16a. The illumination light from the light source apparatus 16 is supplied to the endoscope 31 and illuminates the diseased part or the like in the abdomen of the patient 48 into which the insertion section of the endoscope 31 is inserted.

Further, the central display panel 19, an operation panel 20, and the like are placed on the trolley 11. The central display panel 19 is display means capable of selectively displaying all data during a surgical operation. The operation panel 20 is configured by a display section such as a liquid crystal display and, for example, a touch sensor integrally provided on the display section and is a central operation apparatus operated by a nurse or the like present in an unsterilized region. Operation information instructed by the operation panel 20 is inputted to the system controller 21. Control of the respective apparatuses connected to the system controller 21 is performed.

The control of the respective apparatuses connected to the system controller 21 is not only performed from the operation panel 20 by the nurse or the like present in the unsterilized region. The system controller 21 can recognize voice inputted from a microphone 33 and control the respective apparatuses according to voice of a surgeon present in the sterilized region.

Note that, in FIG. 1, the medical system 1 provided in the operating room where endoscopic surgical operation is performed is illustrated. However, a use of the medical system 1 is not limited to the endoscopic surgical operation. The medical system 1 may be used for other kinds of surgical operation and medical examinations. The medical system 1 may be provided in a room other than the operating room such as a consulting room. The medical system 1 may further include various apparatuses and facilities not shown in FIG. 1. The medical system 1 may include, for example, a video tape recorder (VTR) that records an endoscopic image and the like. The system controller 21 may control the apparatuses and the facilities.

Figure 2:
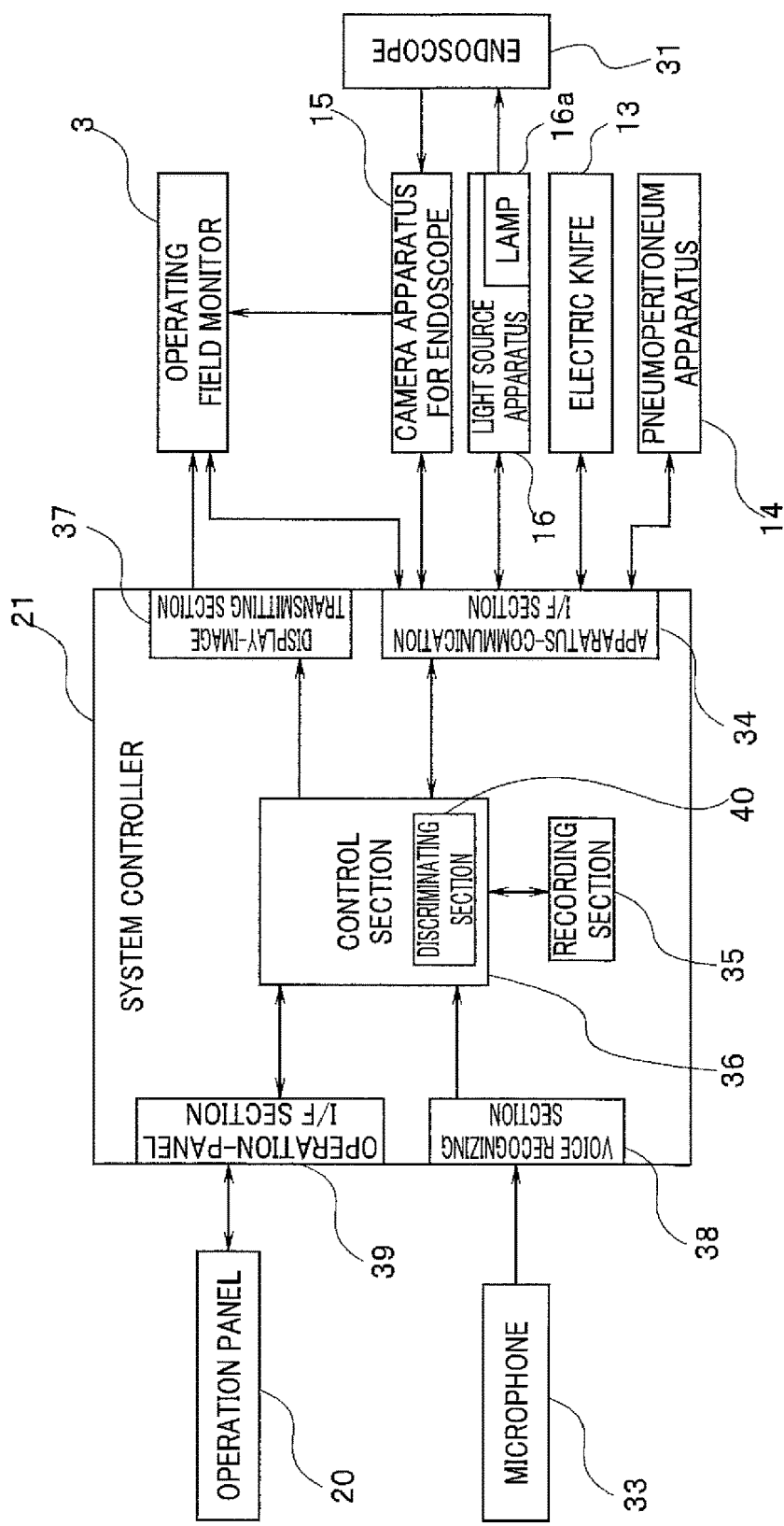
FIG. 2 is a diagram for explaining a detailed configuration of a system controller 21.

A detailed configuration of the system controller 21 is explained with reference to FIG. 2. FIG. 2 is a diagram for explaining the detailed configuration of the system controller 21. As shown in FIG. 2, the system controller 21 includes an apparatus communication interface section (hereinafter referred to as apparatus-communication I/F section) 34 that performs communication between the system controller 21 and the controlled apparatuses such as the operating field monitor 3, the electric knife apparatus 13, the pneumoperitoneum apparatus 14, the camera apparatus for endoscope 15, and the light source apparatus 16 and an operation-panel interface section (hereinafter referred to as operation-panel I/F section) 39 that performs communication between the system controller 21 and the operation panel 20. The system controller 21 includes a recording section 35 in which setting values and various parameters of the controlled apparatuses, data of a screen outputted to the operating field monitor 3, and the like are stored, a control section 36 that controls an operation of the entire system controller 21, a display-image transmitting section 37 that transmits an image to be displayed to the operating field monitor 3, and a voice recognizing section 38 that recognizes voice inputted from the microphone 33.

Various data and setting parameters are inputted to the apparatus-communication I/F section 34 from the controlled apparatuses connected to the system controller 21 and capable of being centrally controlled. A video signal obtained by processing, with the camera apparatus for endoscope 15, an optical image of the diseased part or the like in the body cavity of the patient picked up by the endoscope 31 is inputted to the apparatus-communication I/F section 34. The data, the parameters, the video signal, and the like are outputted to the control section 36. Further, the apparatus-communication I/F section 34 outputs new setting parameters and the like generated by the control section 36 in order to operate the controlled apparatuses to a predetermined controlled apparatus.

In the recording section 35, for example, various data and parameters necessary for execution of a program for causing the system controller 21 to operate and other programs and data for configuring a screen to be displayed on the operating field monitor 3 are stored.

The voice recognizing section 38 identifies, on the basis of voice from the surgeon inputted to the microphone 33, voice for performing operation of the controlled apparatuses connected to the system controller 21 and enabled to be centrally controlled.

Various data, setting parameters, and the like are inputted to the control section 36 from the controlled apparatuses via the apparatus-communication I/F 34. Voice operation information for the controlled apparatuses is inputted to the control section 36 from the voice recognizing section 38. Operation information for the controlled apparatuses is inputted to the control section 36 from the operation-panel I/F section 39. Further, the control section 36 includes a discriminating section 40 that discriminates whether the lamp 16a of the light source apparatus 16 is lit. The control section 36 configures, on the basis of a discrimination result of the discriminating section 40, a screen to be displayed on the operating field monitor 3, outputs the screen to the operating field monitor 3 via the display-image transmitting section 37, and causes the operating field monitor 3 to display the screen.

Note that an endoscopic image is inputted to the operating field monitor 3 from the camera apparatus for endoscope 15 besides the input from the display-image transmitting section 37. When there is no input from the display-image transmitting section 37, the endoscopic image inputted from the camera apparatus for endoscope 15 is displayed on the operating field monitor 3. When there is the input from the display-image transmitting section 37, a screen is displayed according to input content.

Figure 3:
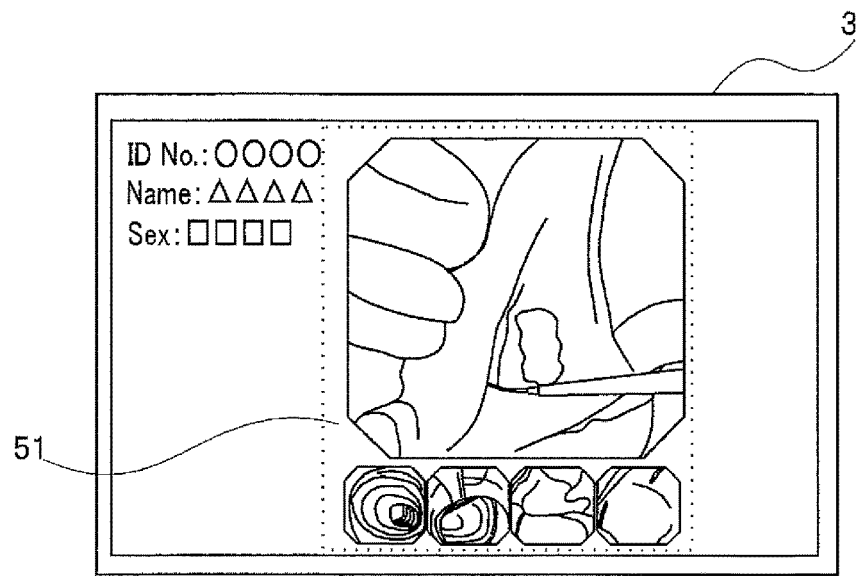
FIG. 3 is a diagram for explaining an example of an operating field monitor 3 on which only an endoscopic image is displayed.
Figure 4:
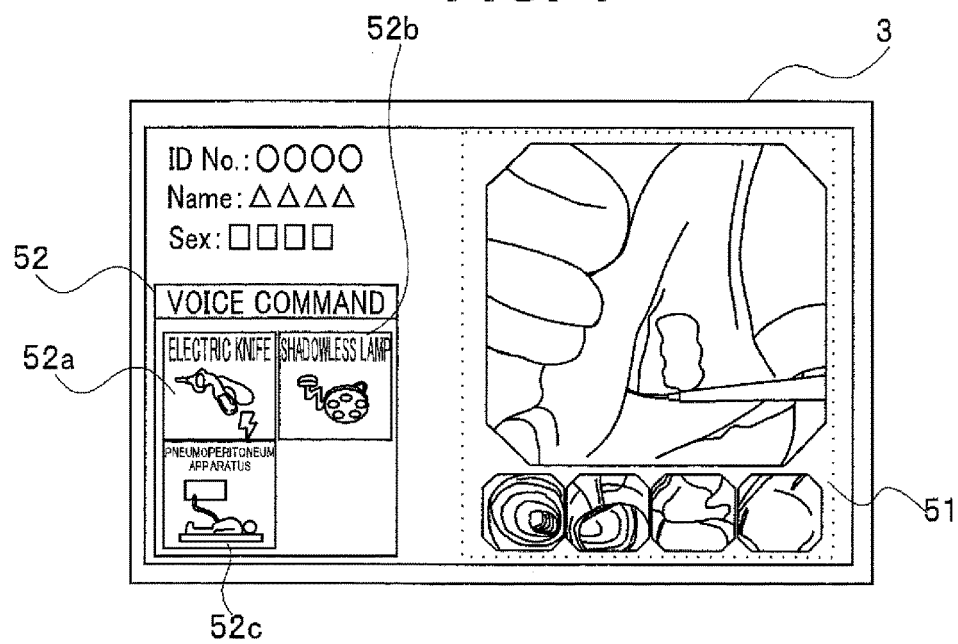
FIG. 4 is a diagram for explaining an example of the operating field monitor 3 on which a voice operation main screen and the endoscopic image are displayed.
Figure 5:
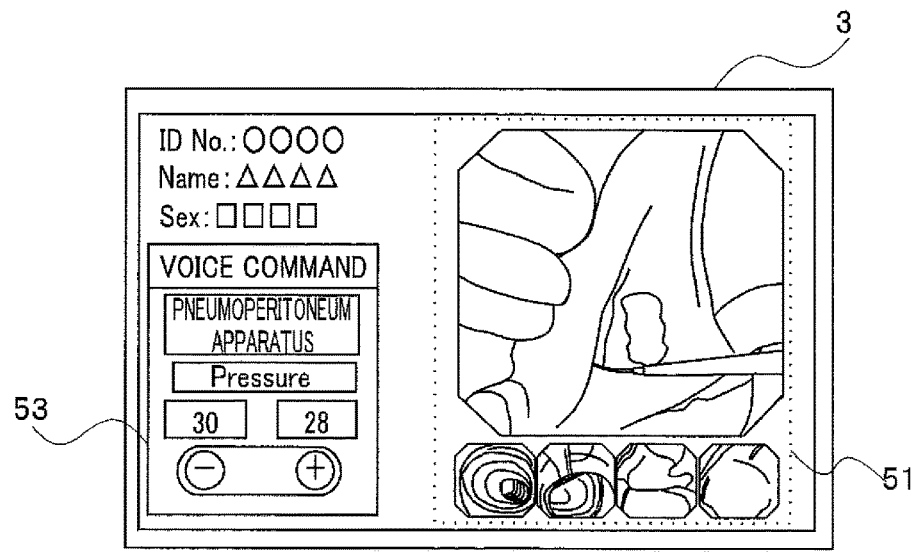
FIG. 5 is a diagram for explaining an example of the operating field monitor 3 on which a voice operation subscreen and the endoscopic image are displayed.
Figure 6:
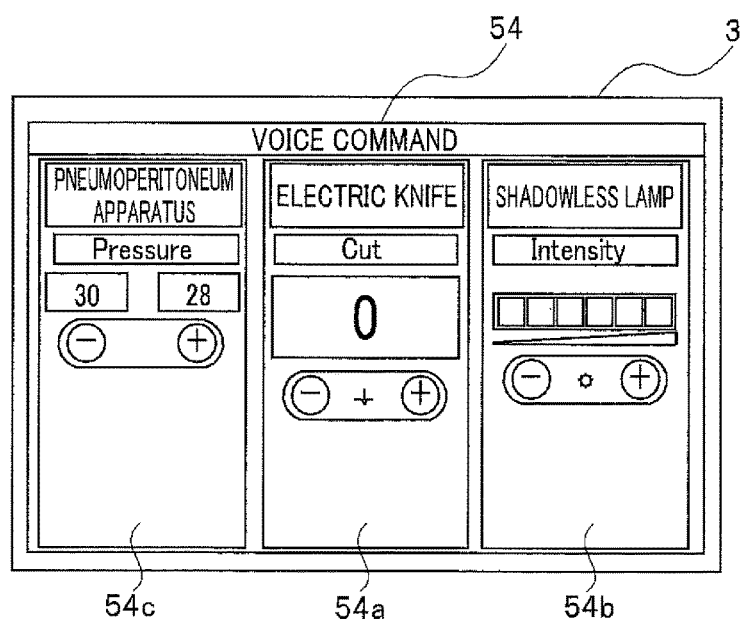
FIG. 6 is a diagram for explaining an example of the operating field monitor 3 on which only a voice operation screen is displayed.

That is, different screens such as a discrimination result of the discriminating section 40 are displayed on the operating field monitor 3 according to situations. The screens displayed on the operating field monitor 3 are explained with reference to FIG. 3 to FIG. 6. FIG. 3 shows an example of the operating field monitor 3 on which only an endoscopic image is displayed. FIG. 4 shows an example of the operating field monitor 3 on which a voice operation main screen and the endoscopic image are displayed. FIG. 5 shows an example of the operating field monitor 3 on which a voice operation sub-screen and the endoscopic image are displayed. FIG. 6 shows an example of the operating field monitor 3 on which only a voice operation screen is displayed.

When it is discriminated by the discriminating section 40 that the lamp 16*a* of the light source apparatus 16 is lit and a voice input to the effect that operation of the controlled apparatuses is performed by voice is not made to the voice recognizing section 38 (when the operation of the controlled apparatuses is performed using the operation panel 20), a screen shown in FIG. 3 is displayed on the operating field monitor 3. That is, an endoscopic image 51 is displayed in the center of the operating field monitor 3. Basic information concerning a patient such as a patient ID, a name, and sex is displayed in a space other than a display region of the endoscopic image 51.

When it is discriminated by the discriminating section 40 that the lamp 16*a* of the light source apparatus 16 is lit and a voice input to the effect that the operation of the controlled apparatuses is performed is made to the voice recognizing section 38, a screen shown in FIG. 4 is displayed on the operating field monitor 3. That is, the endoscopic image 51 displayed in the center of the operating field monitor 3 in FIG. 3 moves to one side of the screen (in FIG. 4, the right side direction of the screen). A voice operation main screen 52 functioning as a first operation instruction screen for instructing the operation of the controlled apparatuses is displayed in a space (in FIG. 4, a region on the left side of the endoscopic image 51) other than the display region of the endoscopic image 51.

The controlled apparatuses operable by a voice input are displayed on the voice operation main screen 52 as a menu. For example, when the electric knife apparatus 13, the shadowless lamp 6, and the pneumoperitoneum apparatus 14 are operable by a voice input, as shown in FIG. 4, three command areas, that is, a command area 52*a* for an electric knife, a command area 52*b* for a shadowless lamp, and a command area 52*c* for a pneumoperitoneum apparatus are displayed on the voice operation main screen 52.

In a state in which the voice operation main screen 52 is displayed, when an operation to be operated is selected, the operating field monitor 3 is automatically switched to a screen shown in FIG. 5. That is, while the display of the endoscopic image 51 and the basic information concerning the patient is kept, the voice operation main screen 52 is switched to a voice operation sub-screen 53. The voice operation sub-screen 53 is a third operation instruction screen for instructing operation concerning the apparatus selected on the voice operation main screen 52. In FIG. 5, an example of the voice operation sub-screen 53 in the case in which the pneumoperitoneum apparatus 14 is selected is shown. On the voice operation sub-screen 53, a present state (setting values, measurement values, etc.) of the selected apparatus is displayed. Therefore, the surgeon can raise and lower a pressure setting value of the pneumoperitoneum apparatus 14 with a voice input and set the pressure setting value to a desired value while referring to the present state displayed on the screen.

Note that, when it is discriminated by the discriminating section 40 that the lamp 16*a* of the light source apparatus 16 is not lit, nothing is displayed on the operating field monitor 3. When a voice input to the effect that the operation of the controlled apparatuses is performed is made to the voice recognizing section 38, a screen shown in FIG. 6 is displayed on the operating field monitor 3. That is, only a voice operation screen 54, which is a second operation screen for performing a check of operation states of the controlled apparatuses and an operation instruction, is displayed on the operating field monitor 3.

On the voice operation screen 54, the controlled apparatuses operable by a voice input are displayed as a menu and present states (setting values, measurement values, etc.) are also displayed concerning the respective controlled apparatuses. For example, when the electric knife apparatus 13, the shadowless lamp 6, and the pneumoperitoneum apparatus 14 are operable by a voice input, as shown in FIG. 6, a command area 54*a* concerning the electric knife apparatus 13, a command area 54*b* concerning the shadowless lamp 6, and a command area 54*c* concerning the pneumoperitoneum apparatus 14 are displayed on the voice operation screen 54. The present states of the respective apparatuses are displayed in the respective command areas 54*a*, 54*b*, and 54*c*. The surgeon can select an operation target apparatus with a voice input and instruct desired operation while checking the present states displayed on the screen.

Figure 7:
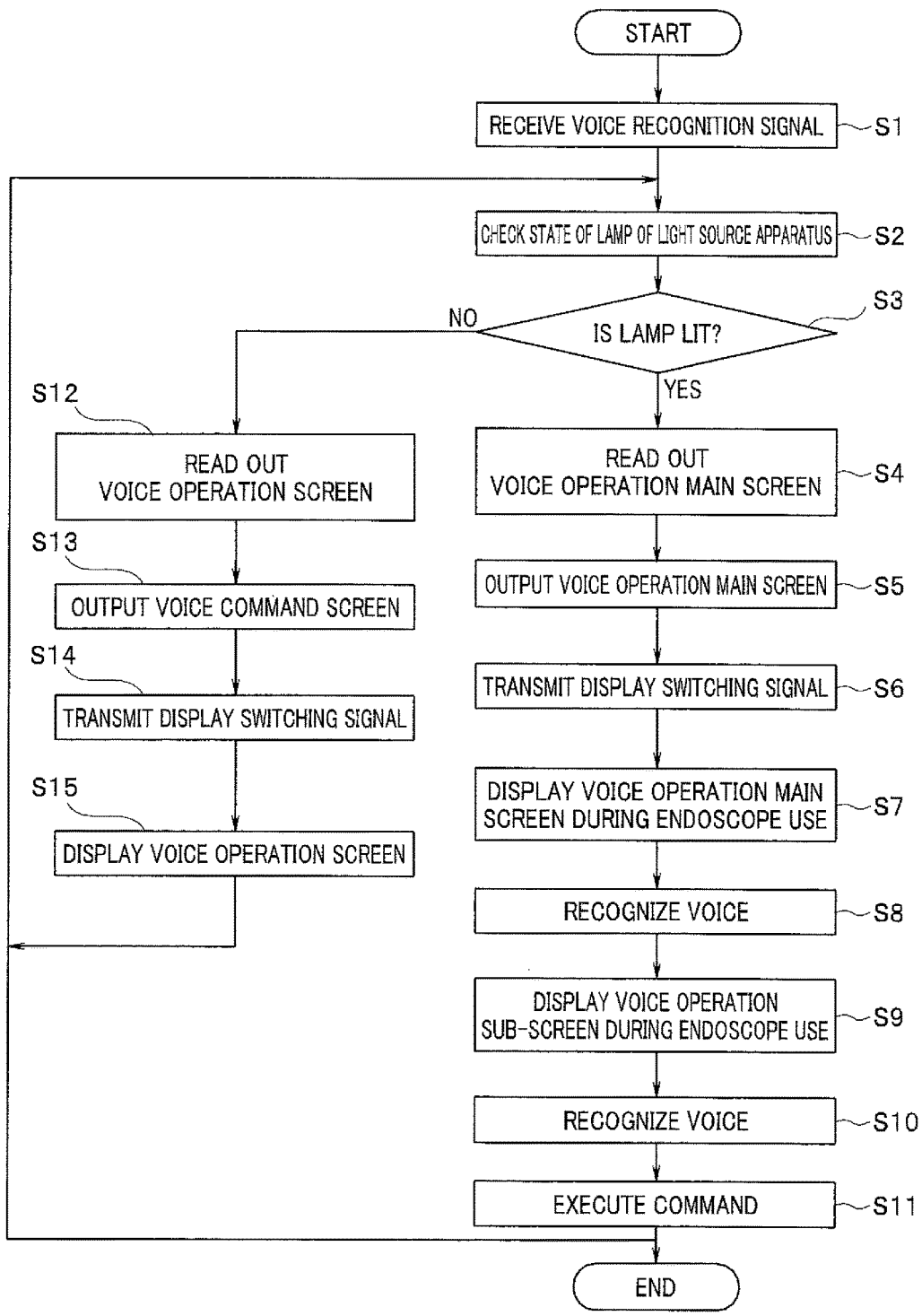
FIG. 7 is a flowchart for explaining an operation procedure of a controlled apparatus and screen switching of the operating field monitor 3.

Operation of a controlled apparatus and screen transition of the operating field monitor 3 in the medical system 1 in the present embodiment are explained with reference to FIG. 7. FIG. 7 is a flowchart for explaining an operation procedure of a controlled apparatus and screen switching of the operating field monitor 3.

First, a surgical operation is started in a state in which nothing is displayed on the operating field monitor 3. When a video signal obtained by processing, with the camera apparatus for endoscope 15, an optical image of a diseased part or the like in the body cavity of the patient picked up by the endoscope 31 is inputted to the system controller 21, the endoscopic image 51 shown in FIG. 3 is displayed on the operating field monitor 3. In this state, when the surgeon utters a predetermined keyword serving as a trigger for starting voice operation such as "menu" and the voice recognizing section 38 recognizes the voice via the microphone 33, the controlled apparatus changes to a state in which the controlled apparatus is operable by a voice input (step S1).

Subsequently, the discriminating section 40 of the control section 36 of the system controller 21 checks a lighting state of the lamp 16*a* of the light source apparatus 16 (step S2). When it is discriminated that the lamp 16*a* of the light source apparatus 16 is not lit (No in step S3), the control section 36 of the system controller 21 generates the voice operation screen 54 using the data and the like stored in the recording section 35 (step S12). The generated voice operation screen 54 is outputted to the operating field monitor 3 via the display-image transmitting section 37 (step S13).

The control section 36 of the system controller 21 transmits a display switching signal for a screen to the operating field monitor 3 via the apparatus-communication I/F section 34 (step S14). When receiving the display switching signal from the system controller 21, the operating field monitor 3 disposes the voice operation screen 54 inputted in step S13 in a region where the endoscopic image 51 has been disposed and displays a voice operation screen during endoscope nonuse (e.g., the screen shown in FIG. 6) (step S15). When only the voice operation screen 54 is displayed on the operating field monitor 3, processing returns to step S2 and a state of the lamp 16a of the light source apparatus 16 is checked.

On the other hand, when it is discriminated that the lamp 16a is lit (YES in step S3), the control section 36 of the system controller 21 generates the voice operation main screen 52 using the data and the like stored in the recording section 35 (step S4). The generated voice operation main screen 52 is outputted to the operating field monitor 3 via the display-image transmitting section 37 (step S5).

The control section 36 of the system controller 21 transmits a display switching signal for a screen to the operating field monitor 3 via the apparatus-communication I/F section 34 (step S6). When receiving the display switching signal from the system controller 21, the operating field monitor 3 adjusts a display position of the endoscopic image 51, disposes the voice operation main screen 52 inputted in step S4 in a region where the endoscopic image 51 is not displayed, and displays a voice operation main screen during endoscope use (e.g., the screen shown in FIG. 4) (step S7).

Subsequently, when the surgeon selects a specific apparatus with a voice input out of the controllable apparatuses displayed on the voice operation main screen 52 of the operating field monitor 3 and the voice recognizing section 38 recognizes the voice (step S8), the voice operation main screen 52 displayed on the operating field monitor 3 is switched to the voice operation sub-screen 53 concerning the selected apparatus. A voice operation sub-screen during endoscope use is displayed on the operating field monitor 3 (step S9).

In step S9, more specifically, first, the control section 36 of the system controller 21 generates, using the data and the like stored in the recording section 35, the voice operation sub-screen 53 concerning the apparatus specified by the voice input. Subsequently, the generated voice operation sub-screen 53 is outputted to the operating field monitor 3 via the display-image transmitting section 37 instead of the voice operation main screen 52. Finally, when the voice operation sub-screen 53 is inputted from the system controller 21, the operating field monitor 3 disposes the voice operation sub-screen 53 in a region where the voice operation main screen 52 has been disposed and displays a voice operation sub-screen during endoscope use.

For example, when the surgeon utters a predetermined keyword (e.g., "pneumoperitoneum apparatus") serving as a trigger for starting voice operation of the pneumoperitoneum apparatus 14 and the voice recognizing section 38 recognizes the voice via the microphone 33 in step S8, the processing proceeds to step S9 and, for example, the screen shown in FIG. 5 is displayed on the operating field monitor 3.

Subsequently, when the surgeon instructs desired operation with a voice input concerning the apparatus displayed on the voice operation sub-screen 53 and the voice recognizing section 38 recognizes the voice (step S10), the control section 36 outputs a control signal to a predetermined apparatus via the apparatus-communication I/F section 34 to execute the instructed operation on a target apparatus (step S11).

For example, when the pneumoperitoneum apparatus 14 is selected as an operation target by a voice input, when the surgeon utters a keyword of operation for raising pressure from a present setting value such as "up" and the voice recognizing section 38 recognizes the voice via the microphone 33 in step S10, the processing proceeds to step S11. The control section 36 outputs a control signal to the pneumoperitoneum apparatus 14 to raise a pressure value from the present setting value by a predetermined value. According to the series of processing explained above, the operation of the controlled apparatus by the voice input is ended.

In this way, according to the present embodiment, a lighting state of the lamp 16a of the light source apparatus 16 is identified by the discriminating section 40 and, when the lamp 16a is lit, the display of the operating field monitor 3 is automatically switched to cause the operating field monitor 3 to display the endoscopic image 51 and the operation screen for the controlled apparatuses together. Therefore, the surgeon can operate the controlled apparatuses by himself/herself without looking away from the endoscopic image 51. It is possible to improve operability.

Note that, in the explanation in the embodiment, the surgeon present in the clean region operates the controlled apparatuses by himself/herself through the voice recognition. However, the operation of the controlled apparatuses is not limited to by the voice. Other methods such as visual line recognition and gesture recognition may be used.

In the embodiment, the control concerning whether the endoscopic image 51, the voice operation main screen 52, and the voice operation sub-screen 53 are displayed together or only the voice operation screen 54 is displayed on the operating field monitor 3 is performed according to the lighting state of the lamp 16a of the light source apparatus 16. The display of the operating field monitor 3 only has to be controlled to be automatically switched by discriminating whether the endoscopic image 51 is acquired and outputted to the operating field monitor 3. Therefore, the switching of the display is not performed according to only the lighting state of the lamp 16a. The switching of the display may be performed according to, for example, presence or absence of an input of a video signal from the camera apparatus for endoscope 15.

Further, in the embodiment, two layers of input screens for voice operation are provided during the display of the endoscopic image 51 to make it possible to select the control target apparatus on the voice operation main screen 52 and perform a specific operation instruction on the voice operation sub-screen 53. The input screens for voice operation are not limited to the two layers and may be provided in three or more layers and sequentially switched and displayed.

The respective "sections" in this specification are conceptual sections corresponding to the respective functions of the embodiment and do not always correspond to specific hardware and software routines in a one-to-one relation. Therefore, in this specification, the embodiment is explained assuming imaginary circuit blocks (sections) having the respective functions of the embodiment. Execution order of the respective steps of the respective procedures in the present embodiment may be changed, a plurality of steps may be simultaneously executed, or the steps may be executed in different order in every execution as long as the execution is not against characteristics of the steps. Further, all or a part of the respective steps of the respective procedures in the present embodiment may be realized by hardware.

The several embodiments of the present invention are explained above. However, these embodiments are illustrated as examples and are not intended to limit the scope of the invention. These new embodiments can be implemented in other various forms. Various omissions, replacements, and changes can be made in a range not departing from the spirit of the invention. These embodiments and modifications of the embodiments are included in the scope and the gist of the invention and included in the inventions described in claims and a scope of equivalents of the inventions.

With the medical system of the present invention, the surgeon can simultaneously refer to a medical image and an operation screen on the operating field monitor. It is possible to improve operability.

The present invention is not limited to the embodiment explained above. Various changes, alterations, and the like are possible in a range in which the gist of the present invention is not changed.

What is claimed is:

1. A medical system comprising:
a light source apparatus configured with a light source to supply light into a body cavity for obtaining an endoscopic image;
a display apparatus configured to display the endoscopic image; and
a processor configured to:
determine whether the endoscopic image is inputted to the processor,
in response to the endoscopic image being inputted to the processor, display an endoscopic image and a first screen on the display apparatus, the first screen including at least one operator-selectable option for selecting one of a plurality of third screens, the third screens having user-selectable controls for controlling one or more operations of controlled apparatuses, and
in response to the endoscopic image being not inputted to the processor, display a second screen on the display apparatus, the second screen including operation states of the controlled apparatuses and user-selectable controls for controlling one or more operations of the controlled apparatuses.

2. The medical system according to claim 1, wherein, when the processor determines that the endoscopic image is inputted to the processor, the processor moves a display position of the endoscopic image on the display apparatus.

3. The medical system according to claim 1, wherein the processor disposes the first screen in a region where the endoscopic image is not inputted.

4. The medical system according to claim 1, wherein, when one of the controlled apparatuses is selected in a state in which the first screen is displayed on the display apparatus, the processor displays, on the display apparatus, one of the plurality of third screens including an operation state concerning the selected controlled apparatus and user-selectable controls for controlling one or more operations of the selected controlled apparatus.

5. The medical system according to claim 4, wherein, when the one controlled apparatus is selected in the state in which the first screen is displayed on the display apparatus, the processor displays the one of the plurality of third screens on the display apparatus instead of the first screen.

6. The medical system according to claim 1, wherein the processor is further configured to:
receive a voice input, and
control the controlled apparatuses according to the voice input.

7. The medical system according to claim 6, wherein, when a predetermined voice is inputted to the processor, the processor determines whether the endoscopic image is inputted to the processor after receiving the predetermined voice.

8. A medical system comprising:
a light source apparatus configured with a light source to supply light into a body cavity for obtaining an endoscopic image;
a display apparatus configured to display the endoscopic image; and
a processor configured to:
determine whether the endoscopic image is inputted to the processor, and
in response to the endoscopic image being not inputted to the processor, display a screen on the display apparatus, the screen including operation states of controlled apparatuses and user-selectable controls for controlling one or more operations of the controlled apparatuses.

* * * * *